United States Patent
Valenti

(10) Patent No.: US 10,448,821 B2
(45) Date of Patent: Oct. 22, 2019

(54) METHOD AND DEVICE FOR DETECTION AND ASSESSMENT OF MARIJUANA IMPAIRMENT

(71) Applicant: Denise A. Valenti, Quincy, MA (US)

(72) Inventor: Denise A. Valenti, Quincy, MA (US)

(*) Notice: Subject to any disclaimer, the term of this patent is extended or adjusted under 35 U.S.C. 154(b) by 298 days.

(21) Appl. No.: 15/297,886

(22) Filed: Oct. 19, 2016

(65) Prior Publication Data

US 2017/0105669 A1    Apr. 20, 2017

Related U.S. Application Data

(60) Provisional application No. 62/243,933, filed on Oct. 20, 2015.

(51) Int. Cl.
*A61B 3/02* (2006.01)
*A61B 3/10* (2006.01)
*A61B 3/00* (2006.01)
*A61B 3/06* (2006.01)

(52) U.S. Cl.
CPC .......... *A61B 3/0041* (2013.01); *A61B 3/0025* (2013.01); *A61B 3/02* (2013.01); *A61B 3/06* (2013.01)

(58) Field of Classification Search
CPC ....... A61B 3/103; A61B 3/1225; A61B 3/024; A61B 3/032; A61B 3/1015
USPC .................. 351/239, 200, 205, 246, 221–222
See application file for complete search history.

(56) References Cited

U.S. PATENT DOCUMENTS

| | | | | |
|---|---|---|---|---|
| 7,771,052 B2 * | 8/2010 | Kratzer | .................... | A61B 3/06 351/205 |
| 9,376,017 B2 | 6/2016 | Bailey et al. | | |
| 2007/0166675 A1 * | 7/2007 | Atkins | .................... | G09B 5/06 434/236 |
| 2011/0304465 A1 * | 12/2011 | Boult | .................... | B60K 28/06 340/576 |
| 2015/0126899 A1 * | 5/2015 | Ghajar | .................... | G09B 5/02 600/558 |

OTHER PUBLICATIONS

Canadian Centre on Substance Abuse, "What Canadian Youth Think about Cannabis," Sep. 2013, 4 pages.
Adams, "Evidence for acute effects of alcohol and marijuana on color discrimination," Perception & Psychophysics, 1976, vol. 20(2), 119-124.
Adams et al., "Influence of Socially Used Drugs on Vision and Vision Performance," Annual Rept. 1974-1975, 1 page.

(Continued)

*Primary Examiner* — Dawayne Pinkney
(74) *Attorney, Agent, or Firm* — Patterson Thuente Pedersen, P.A.

(57) ABSTRACT

A method of identifying individuals impaired by a psychoactive substance such as cannabis. The method includes presenting monocularly to a subject being tested; to each eye separately, a sinusoidal grating pattern of fixed spatial frequency with achromatic contrast or color contrast between grating stripes being temporally alternately modulated at a temporal frequency that ranges between 10 Hz and 60 Hz with a pattern of the contrast being such that the subject being tested can see a frequency doubling in the grating pattern.

20 Claims, 4 Drawing Sheets

(56) References Cited

OTHER PUBLICATIONS

Asbridge, "Acute cannabis consumption and motor vehicle collision risk: systematic review of observational studies and meta-analysis," BMJ, 2012, 344, pp. 1-9.
Bosker et al., "A placebo-controlled study to assess Standarized Field Sobriety Test performance during alcohol and cannabis intoxication in heavy cannabis users and accuracy of point of collection testing devices for detecting THC in oral fluid," Psychopharmacology, 2012, 223:439-446.
Brady et al, "Trends in Alcohol and Other Drugs Detected in Fatally Injured Drivers in the United States, 1999-2010," Am J of Epidemiol. 2014, vol. 179(6) 692-699.
Brown et al., "Pupil Size After Use of Marijuana and Alcohol," Smith-Kettlewell Institute of Visual Sciences, 1977, 1 page.
Citek et al., "Effects of Cannabis Intoxication on Eye Movements and Other Physiological Indicators," American Academy of Optometry, 2012, 2 pages.
Citek et al., "Nystagmus testing in intoxicated individuals," Optometry, vol. 74, No. 11, Nov. 2003, 695-710.
Compton et al., "Results of the 2007 National Roadside Survey of Alcohol and Drug Use by Drivers," NHTSA National Center for Statistics and Analysis, Jul. 2009, 5 pages.
Henderson et al., "Near Peripheral Motion Contrast Threshold Predicts Older Drivers' Driving Simulator Performance," Proceedings of the Fifth International Driving Symposium on Human Factors in Driver Assessment, Training and Vehicle Design, Jan. 2013, pp. 334-341.
Henderson et al, "Two-Minute Peripheral Motion Contrast Threshold Test Predicts Older Drivers' Collisions and Hazardous Driving in Simulator," Jun. 2013, 1 page.
Schwitzer et al., "Association Between Regular Cannabis Use and Ganglion Cell Dysfunction," JAMA Ophthalmology, Dec. 8, 2016, pp. E1-E7.
Schwitzer et al., "Transient Retinal Dysfunctions after Acute Cannabis Use," European Addiction Research, Jul. 5, 2016, pp. 287-291.
Valenti, "Alzheimer's Disease: Frequency Doubling Technology Biomarkers in the Visual System," ARVO Annual Meeting Abstract, Mar. 2012, vol. 53, Issue 14, 2 pages.
Valenti, "Alzheimer's Disease: Screening Biomarkers Using Frequency Doubling Technology Visual Field," ISRN Neurology, Aug. 6, 2013, vol. 2013, 9 pages.
Valenti, "Functional Losses in Parkinson's Disease: Frequency Doubling Technology," ARVO Annual Meeting Abstract, May 2005, 1 page.
Valenti et al., "Movement Disorders: Deficits in Visual Processing as Measured by Frequency Doubling Technology," ARVO Annual Meeting Abstract, Apr. 2009, 1 page.
Valenti, "Retinal Inhibition Secondary to Methotrexate: Identified With Frequency Doubling Technology," ARVO Annual Meeting Abstract, May 2006, 2 pages.
Venkataraman et al., "Choice of Grating Orientation for Evaluation of Peripheral Vision", Optometry and Vision Science, vol. 93, No. 6, Jun. 2016, pp. 1-8.

* cited by examiner

METHOD AND DEVICE FOR DETECTION AND ASSESSMENT OF MARIJUANA IMPAIRMENT

CLAIM TO PRIORITY

This Application claims the benefit of U.S. Provisional Application 62/243,933 filed on Oct. 20, 2015 entitled "Impairment Measurement: Marijuana and Driving: Method and Device for Detection and Assessment of Marijuana Impairment" the entire content of which is incorporated herein by reference.

FIELD OF THE INVENTION

The invention relates to testing for functional impairment arising from the consumption of cannabis and other psychoactive drugs. More particularly the invention relates to testing for impairment caused by the consumption of such substances to identify individuals who are impaired for driving and other tasks.

BACKGROUND OF THE INVENTION

There are limited options available to detect impairments impacting driving when impairment is due solely to cannabis use or the use of other psychoactive drugs. In a 2007 roadside survey more drivers were positive for drugs than alcohol (NHTS 2007) and this contributes to the risk of accidents when driving. Cannabis users suffer auto injury ten times more frequently than non-users. (ScienceDaily) Eleven percent of those presenting in an emergency room after an auto accident were found to have used cannabis in the absence of other drugs or alcohol and acute cannabis consumption presents a risk for motor vehicle crash and fatal collisions involving motor vehicles. (Asbridge 2013)

A survey of drivers in Canada found that 4.8 percent of drivers admitted to driving within two hours of using cannabis. (Porath 2013) With the current legalization of cannabis for recreational use in several states, the rate of automobile injury secondary to cannabis intoxication is likely to increase.

The state of Colorado has the most experience within the United States, with cannabis use and driving. Starting Jan. 1, 2014 Amendment 64 took effect allowing for the legal use of recreational cannabis in the state of Colorado for citizens over the age of twenty one. Even though the laws in Colorado clearly state that it is illegal to drive high, twelve percent of the citations issued in 2014 for DUI involved cannabis use. The DUI fatality rate increased by 6 percent in 2014, and the rate of DUI citations increased by 23 percent compared to 2013. Of the total citations issued, over six percent were suspected to involve only cannabis and no other substances. Colorado officials take the position that any amount of cannabis can impair a person for driving and DUI citations can be based on observations. Colorado has established a legal level of cannabis that is considered to impair driving function at five nanograms of active tetrahydrocannabinol, the component impacting cognitive function, per milliliter of whole blood. (Blood) Other states have adopted a zero tolerance level and there is research supporting this that indicates how little cannabis is required to significantly impair skills required for driving. (Impair) The Colorado Department of Transportation did a survey on the attitudes and behaviors of residents several months before recreational cannabis became legal. They found that twenty percent of the respondents that had used cannabis in the previous year had driven shortly after consuming cannabis and those that did so within two hours drove on average seventeen times during a month. (CDOTNEWS) Colorado invested one million dollars on a public education campaign, "Drive High, Get DUI", in an effort to minimize the impact of driving while impaired secondary to cannabis. (Education) Even after the campaign a survey found that 57% of those reporting to use cannabis, drove within two hours of consumption. (CDOT57)

Washington State has had legal marijuana for a shorter period, but still is reporting significant problems with increasing numbers of impaired drivers due to cannabis consumption. A report (Survey) for the Washington Traffic Safety Commission in a survey conducted by the Pacific Institute for Research and Evaluation found that seventy percent of drivers questioned had used cannabis and of those reporting use 44% acknowledged they had driven a car less than two hours after using cannabis. Further 90% of those who drove while using cannabis, did not feel that cannabis impaired their ability to drive. In the year 2012 there were 988 driver tests that came back positive for cannabis and this increased to 1, 362 in 2013. (KXLY) From 2009 through 2013, more than 1,000 people died in impaired driving collisions in Washington. Impaired driving is involved in nearly half of all traffic deaths and more than 20 percent of serious injury collisions. (Kirkland) When cannabis is combined with alcohol the effect is more deadly than alcohol alone. Alcohol intoxication increases the risk of a fatal accident by thirteen times compared to a sober driver but alcohol and cannabis intoxication increases the risk twenty four times. (Brady)

The National Institute on Drug Abuse prepared a White Paper on drugged driving research in 2011 that discussed marijuana use; "For illegal drugs, Zero Tolerance (ZT) per se laws are those which set that limit at the drug detection cut-off level. In concept it is not necessary to prove driver impairment to convict an offender under a per se law." (NIDA/Whitehouse} They further discussed per se drugged driving laws, "A per se drugged driving law is one in which a specified level of a drug in the body of a driver is defined as an offense. This may be a level at which here is evidence that the drug has been shown to effect driver performance such as the 0.08 g/mL limit for alcohol."

There is limited research on cannabis impairment related to driving. Impairment due to cannabis differs significantly than the impairments caused by alcohol. Even small amounts detected in the blood have been shown to impair the cognitive perceptual functions necessary for safe driving. (Zero). The demonstration of cognitive dysfunction even with small amounts of cannabis is fueling arguments for zero tolerance of cannabis with driving. Fifteen states have zero tolerance regulations when it applies to drug use and cannabis. (Fifteen) While some exclude medical marijuana users, an estimated nine have more absolute laws with zero tolerance applied to all cannabis users.

In a September 2015 report from the Governor's Highway Safety Administration the complexities of evaluating impairment and driving under the influence of cannabis were discussed. Extraordinary attention was paid to cannabis as it is considered to be a threat to public health safety. The report reiterates that driving under the influence of drugs; DUID, is illegal in every state. This is much the same as driving under the influence of alcohol, DUI. Like driving under the influence of alcohol, DUID has two requirements that law enforcement must take into consideration. The driver must exhibit signs of impairment through behavior observed by a law enforcement officer and the impairment must be linked to a drug. An officer must have observed a driver demonstrating impairment. Only then can an officer obtain chemical evidence of a drug, usually through a blood test, and the officer must be able to link drug presence to the observed impairment. If the driver refuses a blood test, the officer relies on observations. All this takes longer than for alcohol. With alcohol use the signs are well understood and backed by years of research. The Standardized Field Sobriety Testing (SFST) is an efficient and accurate screening. Evidence of blood alcohol level can be obtained by the biomarkers present in a breath test. The links between SFST, breath-testing and alcohol impairment are recognized by the judiciary system. Traditional training of law enforcement officers does not always include adequate training to observe impairment to driving that arises from drugs. It can take several hours to obtain the needed legal permissions to draw blood from a driver and there are concerns that blood levels related to cannabis do not always match the impairments. Further drug testing can be expensive with labs having substantial backlogs. Cannabis related driving impairment presents a unique challenge to law enforcement as well as to the court systems. A clear understanding of how cannabis has an impact on the ability to drive and limits on how an officer can compel further testing creates barriers to removing drivers impaired by cannabis consumption from the road. Unless there is evidence of impairment to drive similar to the SFST related to alcohol, an officer cannot require a driver to undergo further evaluations.

When there is a concern related to impairment to drive, police officers use standardized observation techniques. The most common is the SFST. The assessments used in the SFST were developed primarily to determine alcohol related impairment to drive. Currently assessments of the visual system by observation are part of a standardized field sobriety test sequence used to detect alcohol impairment. The standardized field sobriety test sequence is used to detect other impairments; including cannabis.

A part of the SFST is the screening for alcohol related horizontal gaze nystagmus. The horizontal gaze nystagmus related to alcohol occurs when the eyes move from looking straight ahead to the side in a horizontal motion. The observation of a driver's eye movements along the horizontal axis while the driver is fixating a target are subjectively interpreted for the presence of horizontal nystagmus, jerking eye movement, and eye pursuit dysfunctions. If the nystagmus is observed to be present when the eye position is at an angle approximating forty five degrees or less and/or there are losses of fixation during pursuit eye movements there is a high likelihood that the driver has a blood alcohol level that would impair driving.

Horizontal gaze nystagmus testing has been shown to have an accuracy of over 75% in the detection of blood alcohol content of 0.09% or greater in a study undertaken by Dixon and colleagues. (Dixon 2009) Furthermore, studies of horizontal gaze nystagmus have shown the test to be sensitive even if blood alcohol levels are lower than legal limits of 0.08%. Horizontal gaze nystagmus testing, when properly administered is sensitive in blood alcohol levels of 0.04-0.08%. (McKnight 2002) The horizontal nystagmus test is not complex to administer, but it does require significant learned skill to interpret a driver's response. This can create issues when presented in court as the officer's administration and interpretations of the test are subjective. When the signs of horizontal gaze nystagmus occur, there is concern that the blood level is greater than 0.04%. (McKnight 2002) The rate of alcohol related auto accidents is staggering. Over 15,000 deaths associated with alcohol related traffic accidents occur annually, and over 40% of auto fatalities each year are related to alcohol consumption. Cannabis also impairs driving but, unlike alcohol, it is difficult to determine blood levels that cause impairment.

Application of eye movement as an indicator of impairment for cannabis use is inconclusive. Citek and colleagues evaluated 25 participants identified by urinalysis to have cannabis as the only intoxicant and found that there was lack of findings for deficits in eye movements. (Citek 2012) Adams and colleagues found deficits in horizontal gaze nystagmus (HGN) as well as visual tracking with the consumption of cannabis, but not at a level as significant as those seen with intoxication with alcohol. (Adams 1975) Smooth tracking eye movements and saccadic tracking eye movements are reduced with alcohol but not with marijuana or a placebo in the motion study undertaken by Flom and colleagues. (Flom 1976) In a study of 20 adults using cannabis and cannabis combined with alcohol, researchers found that with cannabis alone the users showed impairment with the field sobriety test of one leg stand, but dysfunctions in regards to horizontal gaze nystagmus were when cannabis was combined with alcohol. (Bosker 2012) Accordingly, horizontal gaze nystagmus appears not to be affected by cannabis even though affected by alcohol. One leg standing is uncertain as to its correlation with cannabis consumption.

There are products on the market to test for drug use. One the DrugTrap®, consists of a filter holder, mouthpiece, plastic bag with volume indicators and seals for both ends. The consumer blows into the mouthpiece and then the bag is sealed and mailed to the company for analysis. The product is currently not FDA approved. (DrugTrap) Another product, though not on the market, is a telephone application to record and analyze eye movement scanning with cannabis consumption. This is described by Arizona State University Center for Innovation. (Arizona) A further product, BreathalEyes records eye movements and nystagmus and calculates the probable blood alcohol content of the person using the application on a smart phone or tablet. (BreathalEyes) MyCanary is yet another product. MyCanary is a telephone application that allows a driver to test their own theoretical potential to be too impaired to drive. It utilizes simple cognitive and physical tests including balance, memory, reaction and time perception and provides a readout for the driver. There is no research or science background available on this product and it is not intended to be used by law enforcement or the justice system. (MyCanary) Canary) Background on Retina and Brain Nuclei related to Cannabinoid Receptors The active ingredients in cannabis act on cannabinoid receptors in the human body. The primary cannabinoid receptors that have been identified are classified as either CB1 or CB2 receptors. The CB2 category is highly represented in the central nervous system; including the retina. CB2 receptors are represented in the central nervous system but to a lesser degree than CB1 receptors. CB1 receptors have their greatest prevalence in the periphery and immune systems. In humans there are two primary endogenous compounds acting on the receptors, N-arachidonoylethanolamine (anandamide, AEA) and 2-arachidonoylglycerol (2-AG). Anandamide acts primarily post-synaptically as a retrograde compound to modulate neurotransmitters. Anandamide has greater affinity for CB1 receptors. 2-AG has been found to act pre-synaptically and also has greater affinity for CB1 receptors. 2-AG is found abundantly in the brain, but shows less affinity for CB1 receptors than does Anandamide. (Shwitzer 2015) The receptor sites in the brain related to CB1 and CB2 are primarily those involved in higher cognitive functions. The forebrain, midbrain and hindbrain have areas associated with the control of movement that are affected and hindbrain areas associated with the control of motor and sensory functions of the autonomic nervous system are affected. (Glass 1997) All regions where cannabinoid receptors have been identified have implications for performance related to driving.

The human retina has representation of cannabinoid receptors throughout multiple layers and cell structures. This is supported by animal models. CB1 activity in human retina is evidenced by staining in the synaptic layers of the retina; the inner and outer plexiform layers. The density of CB1 Receptors increases in the inner nuclear layer and the ganglion cell layer. There is substantial staining in the outer segments of the photoreceptors. (Straiker 1999) Research has demonstrated the expression and regulation of CB1 receptors in human retinal pigment epithelium cells. (Wei 2013) An animal model using mice supports this finding with identification of CB1 receptors in the inner retina and ganglion cells, with integrations and processing of excitatory signal from bipolar cells and inhibitory signals from amacrine cells. (Wang 2013) The activation of CB1 receptors differs dependent on the circadian quality of light; night versus daytime. If CB1 receptors are activated during day, the rod-cone gap junctional signaling is decreased. However if activated at night the rod-cone gap junctional signaling is increased. (Jieng ARVO) This has functional implications for scotopic vision and glare recovery.

An additional rodent model has demonstrated that CB2 receptors are localized in cone and rod photoreceptors, horizontal cells, some amacrine cells, and bipolar and ganglion cells. (Cecyre 2013) Additional evidence of CB2 receptors within rodent retina as well as the central nervous system has been identified by additional groups. (Hu 2010) Lu and colleagues identified CB2 evidence in the somas of retina ganglion cells in a rodent model. (Lu 2000) This differs from a primate model which shows that CB2 receptors are in the primate retina but exclusively in the retinal glia, with the model still supporting that CB1 receptors are present in neuroretina. (Bouskilla 2013CB2)

One of the primary brain nuclei involved in processing visual signals is the lateral geniculate nucleus (LGN) and this area of the brain is dense in cannabinoid receptors. A primate model; the vervet monkey, shows that CB1 receptors are located throughout the LGN with prominent findings in the magnocellular layers. The receptors are less prominent, but still evident, in the koniocellular layers. (Javadi 2015) Magnocellular functions involve primarily achromatic signals; related to contrast and temporal functioning of vision. The currently used testing for glaucoma utilizing contrast and temporal functioning is assessing magnocellular processing. Koniocellular functioning involves the processing of chromatic signals in the blue wavelength. Another primate model of CB1 functioning within the LGN shows demonstrated that the active ingredient in cannabis inhibits cells that would normally fire when exposed to light and cells that would be inhibited by light were either unresponsive with no inhibition activity or actually had an increase in excitation. (Bieger 1972) This has significant implications for the interaction of central macular retinal functions and peripheral retinal functions as well as scotopic (night vision or dim light vision) and photopic (daylight vision or bright light vision) functions.

DaSilva and colleagues were able to quantify the functional action on CB1 receptors within the LGN and found two populations; 28% were excited by an antagonist and 72% were inhibited. When activated artificially (as they would be with cannabis) the visual signals were altered. With excitatory activity there was a decrease in the signal to noise ratio but an increase in variability. With altered inhibition; which accounts for over seventy percent of the cells in the LGN, there was an increase in the signal to noise ratio with reductions in variability. The researchers concluded that the abnormal signals originating from the LGN with artificial stimulation of the cannabinoid receptors using cannabis and then traveling to the cortex would account for the behavioral effects of cannabis. (DaSilva 2012) The findings in the LGN support evidence of diverse roles of cannabinoid receptors in both the retina and the LGN, in modulating both excitation of cells and the inhibitory cell functions. The authors hypothesize that the cannabinoid receptor functions within the visual system account for many of the behavioral effects from cannabis. The behavioral effects and changes in cognitive function along visual pathways, demonstrated by functional brain imaging, are enough to impair driving functions. (MRI) A rodent model of development and function of CB1 receptors in the visual cortex found intense staining for CB1 receptors in layers II, III, and VI. The functions were influenced by dark and light cycling and had plasticity related to retinal stimulation. (Yoneda 2013)

Reductions in acuity have been reported secondary to cannabis consumption. (Dawson 1977) Adams and colleagues did not find reductions in static acuity but did find reductions in dynamic acuity after cannabis consumption. (Adams 1975)

The structural findings related to the cones in the retina and koniocellular layers of the LGN offer an explanation for the functional findings of color impairment with cannabis consumption. Several researchers have identified color deficits along the blue axis. Adams and colleagues found dose related impairment with the consumption of cannabis was identified using the Farnsworth-Munsell 100 hue test and the findings were along the blue axis. The deficits were similar to those blue deficits that occur with retinal based pathology leading researchers to conclude that the origin of the dysfunction was in the retina itself (Adams 1976) Dawson and colleagues supported the findings of significantly reduced color vision functions with decreased color matches among those having consumed cannabis. (Dawson 1977) In studies of retinal tissue in vitro; Hu and colleagues found evidence of cannabinoid function in postsynaptic cone bipolar cells that interact with cone photoreceptors providing further physiologic evidence to support the functional deficits in color processing. (Hu 2010)

Early reports in the 1970s indicated that marijuana impacted pupillary function with dose related constrictions of the pupil. (Hepler 1972, Brown 1977) More recent reports using pupilometer technology are documenting dose related dilations of the pupil. (Stark 2003, Merzouki 2008) Dilated pupils as well a slow pupil reaction were reported to be indicators of cannabis consumption by Bramness and colleagues. The diminished pupil reaction persisted for the first two hours. They observed an increase in dilation among those with blood cannabis concentrations above 2.9 ng/ml, but the observation was only present in 35% of those consuming cannabis. (Bramness 2010)

There is evidence of dysfunction related to dark adaptation, light adaptation, glare recovery and photopic functions with the consumption of cannabis. (Dawson 1977, Adams 1978) This may be related to changes in pupil function, suppression of central inhibitory or excitatory retinal functions, abnormal retinal functions peripherally or any combination of the foregoing. The dysfunctions persist for two hours after cannabis consumption. That cannabis impacts central photopic based functions is evidenced by studies that demonstrate increase in scotopic functions. There are reports of improved night vision with the use of cannabis. (Russo 2004) In support of increased peripheral scotopic function is the discovery of a novel exogenous cannabinoid in rod segments and elsewhere in the central nervous system of a primate model, GPR55. (Bouskilla 2013GPR55)

There is room for improvement in the area of testing for functional impairment due to the consumption of cannabis and other psychoactive drugs. There is currently no field applicable test available to identify those driving impaired due cannabis consumption.

SUMMARY OF THE INVENTION

Example embodiments of the invention utilize retinal functioning as a biomarker for impairment to drive after consuming cannabis or other drugs. Embodiments of the invention improve on existing strategies and provides a practical field applicable test.

The technology of embodiments of the invention is a novel and quick psychophysical visual assessment for the detection of functional impairment due to cannabis or other psychoactive drug consumption. Example embodiments of the invention include tests designed for professional administration and self-administration. Self-administered tests may include the utility of vehicle ignition interlock applications to prevent an impaired person from operating a motor vehicle.

Current strategies to detect fitness to drive a vehicle or to operate machinery include the observation of physical dysfunction in the form of field sobriety testing, and are usually performed by law enforcement personnel. The results of such testing correlate well with other biologic measures when the impairing substance is alcohol. Current vehicle ignition interlock applications operate relative to detection of alcohol only. No such device is known to exist for cannabis. The correlation of field sobriety testing to biologic measures with other substances; marijuana and psychoactive drugs is poor. Marijuana, in particular, and other psychoactive drugs impact additional cognitive neuroprocesses that are crucial for the safe operation of a motor vehicle or the operation of machinery, that are not detectable with the physical assessment using existing field sobriety testing.

The visual system is extensively involved in the cognitive functions that are essential for safe operation of a motor vehicle or machinery. The eye's retina has multiple levels of cellular activity that are modulated by cannabis specific receptors as well as receptors specific to other psychoactive drugs. The consumption of cannabis, in particular, inhibits and alters cellular responses within the retina that rely on the neural activity of cannabinoid receptors. A test as applied according to embodiments of the invention specifically measures visual functions that are selectively inhibited by cannabinoid consumption or pathologically overstimulated by cannabis consumption. The test can also indirectly measure the effects of other psychoactive drugs. A test according to embodiments of the invention serves as a noninvasive biomarker of functional cognitive impairment, measured through the visual system, secondary to consumption of cannabis and other psychoactive drugs. Because the distribution of cannabinoid receptors is known throughout the retina, the test parameters are sensitive and specific to cellular functions impaired by cannabis.

The test, according to embodiments of the invention, is indirectly sensitive to other psychoactive drugs. Cognitive dysfunction and in the case of this test; vision impairment, is an indicator of expected impairment that would interfere with safe driving or the operation of machinery. The test, according to embodiments of the invention, provides a noninvasive approach to quickly and accurately assess the functional ability to drive after consuming cannabis.

Example embodiments of the invention include a vision test utilizing achromatic or chromatic frequency doubling visual phenomena. Frequency doubling phenomena are produced by either isoluminent pairs of color visual stimuli in the form of alternating stripes or achromatic visual stimuli in the form of contrasting alternating stripes. This test utilizes visual stimuli consisting of temporally alternating stripes at a rate of between 10 and 60 HZ in a grid series to induce a frequency doubling pattern. The spatial frequency (width of the stripe) varies as well as the temporal frequency (alternations per second) and contrast or saturation. Chromatic stimuli include isoluminant, single wavelength, complementary color pairs, with the isoluminence and/or saturation being variable in that the pairs have variable luminance and/or saturation while remaining matched in luminence. The color pairs may include, for example, blue and yellow or red and green. Isoluminence in this context means that the colors are as close as practical to single wavelength colors.

Achromatic stimuli include pairs of achromatic stripes of variable contrast between pairs. The stimuli are presented within the visual field of each eye separately, one target presentation at a time with the location within the visual field varying from single target presentation to single target presentation, while the test subject fixates on a small stationary fixation target. The presentation of stimuli are organized in such a manner as to measure the appropriate visual field and functionality of visual field impaired by cannabis consumption or other psychoactive drugs, but not in a manner predictable to the test subject.

Stripes may be presented to the eye in a variety of orientations. According to example embodiments of the invention, stripes may be presented peripherally to fixation in orientations parallel to meridians of the eye, perpendicular to the meridians or oblique to the meridians. For the purposes of this disclosure meridians should be considered to be lines that pass generally through the point of fixation or the fovea and that radiate outwardly to the peripheral retina or peripheral visual field.

Stripes may be presented parallel to the meridians of the eye with the intention of taking advantage of the meridional preference effect. Research has demonstrated that stimuli oriented radially, parallel to the meridian, are better resolved than stimuli in other orientations. Accordingly, the eye may demonstrate greater sensitivity to stimuli with meridionally oriented stripes.

Alternatively, if comparison between two striped stimuli is desired, example embodiments of the invention may present stripes at orientations oblique to the ocular meridians. For example stimuli may be presented at angles of plus and minus forty five degrees relative to the meridians. This means that the two stimuli should be perceived with approximately equal sensitivity and facilitate comparison of the two stimuli.

Test strategies include threshold sensitivity as well as simple detection. A test is presented to an individual on a personal type hand held electronic device such as hand held cellular phone or tablet or the like. The test may also be presented on a head worn headset or eyeglass like device as well. The headset may resemble a virtual reality type head worn device and may be used in a situation where control of ambient lighting and brightness is beneficial. A test subject interacts with the electronic device by triggering, for example, a momentary contact switch or a touch of the screen in response to seeing a test stimulus. Test pattern presentation strategy incorporates stimuli that measure both false positive and false negative responses.

I. According to another example embodiment, the invention includes a technology application test method to determine the impairment or decreased function of the visual system secondary to cannabis consumption or other psychoactive drugs. This example embodiment utilizes achromatic test patterns. That is black and white patterns. An example embodiment of the method includes multiple steps as follows:

A. Presenting monocularly to a subject being tested; in each eye separately, an achromatic sinusoidal grating pattern (which is seen by the subject as a pattern of stripes or alternately a grid) of fixed spatial frequency with the contrast between grating stripes being temporally modulated (alternations) at a frequency that ranges between 10 Hz and 60 Hz with the pattern of contrast being such that the subject being tested can see a frequency doubling in the grating pattern.
  1. Decreasing the contrast of the grating pattern presented until a first contrast ratio/value is reached where the frequency doubling in the grating pattern is no longer seen by the test subject.
  2. Further decreasing the contrast of the grating pattern until the contrast ratio/value is well below the test subject's threshold of detection of the ratio/value.
  3. Increasing the contrast of the grating pattern until a second contrast ratio/value is reached where the frequency doubling in the grating pattern is first detectable.
  4. Comparing the first contrast ratio/value and the second contrast ratio/value to those of a normal population who have not consumed cannabis and have no pathology impacting the visual functions tested.
  5. Taking the first contrast ratio/value identified in step A1 and varying the temporal modulation (alterations) from 10 Hz to 60 Hz and determining when the frequency doubling in the grating pattern is first detectable by the test subject.
  6. Taking the second contrast ratio/value identified in step A3 and varying the modulation (alterations) from 10 Hz to 60 Hz and determining when the frequency doubling in the grating pattern is first detectable by the test subject.
  7. Taking the values identified in (A1 through A5) and (A3 through A6) and comparing them to the contrast ratio values combined with temporal values in the modulation (alterations) and comparing them to those of a normal population who have not consumed cannabis and have no pathology impacting the functions tested.
  8. A threshold is determined by a procedure based on Bayesian statistics known as Zippy Estimation of Sequential Testing (ZEST). ZEST uses techniques to combine prior knowledge about the expected distribution of thresholds and the initial probability density function using knowledge obtained from each stimulus presentation. Studies have shown that the advantages offered by this algorithm over other strategies include a 50% reduced test time compared to other threshold strategies, greater efficiency, and lower intra and inter test variability.

B. Another example embodiment of the invention utilizes colored test patterns and includes presenting monocularly to a subject being tested; in each eye separately, a chromatic sinusoidal grating pattern (stripes) with fixed spatial frequency and the chromatic stripes being temporally modulated (alternations of complementary stripes) at a frequency which ranges between 10 Hz and 60 Hz with the pattern of saturation being such that the subject being tested can see a frequency doubling in the pattern. The colors of the chromatic sinusoidal grating pattern are complementary colors with selection from the entire color spectrum. The saturation of the chromatic stripes vary, but the two pairs remain matched in luminence.
  1. Decreasing the saturation of each complementary chromatic pair (examples include: yellow and blue, red and green) until a first saturation ratio/value is identified where the frequency doubling is no longer seen by the test subject.
  2. Further decreasing the saturation of the chromatic grating pattern until the saturation ratio/value is well below the test subject's threshold of detection of the saturation ratio/value.
  3. Increasing the saturation of the grating pattern until a second saturation ratio/value is reached where the frequency doubling in the grating pattern is first detectable.
  4. Comparing the first saturation ratio/value and the second saturation ration to those of a normal population who have not consumed cannabis and have no pathology impacting the visual functions tested.
  5. Taking the values identified in step B1 from the multiple chromatic pairs and varying the individual multiple chromatic pairs temporal modulation (alterations) from 10 Hz to 60 Hz and determining when the frequency doubling in the grating pattern is first detectable to the test subject.
  6. Taking the values identified in step B3 from the multiple chromatic pairs and varying the individual multiple chromatic pairs temporal modulation (alterations) from 10 Hz to 60 Hz and determining when the frequency doubling in the grating pattern is first detectable.
  7. Taking the values identified in (B1 through B5) and (B3 through B6) and comparing them to the contrast ratio values combined with temporal values in the modulation (alterations) and comparing them to those of a normal population who have not consumed cannabis and have no pathology impacting the functions tested.
  8. Threshold is determined by a procedure based on Bayesian statistics known as ZEST as discussed above.

C. In further example embodiment, the application of steps A1-A8 and B1-B8 are performed while varying the spatial frequency of the stripes.

D. In further example embodiment, a professionally administered test has a fixed spatial frequency and a fixed temporal frequency with the contrast or saturation being variable.

E. In further example embodiment, a self-administered test has a fixed spatial frequency and a fixed temporal frequency with the contrast or saturation being variable.

F. In further example embodiment, a self-administered test is operably coupled to a vehicle ignition interlock device whereby the vehicle is disabled if the test indicates impairment.
   1. In further example embodiment, a self-administered test operates in conjunction with a vehicle ignition interlock application that has biometric recognition such as iris recognition whereby the user driving the vehicle is confirmed to be the test subject who has passed the test.
      a. Biometric recognition limits the self-administration of the test to only the operator designated or assigned to the vehicle ignition interlock device.

It is clear that the aforementioned features, as well as those to be described below, can be used not only in the combinations stated, but also in other combinations or in isolation, without leaving the scope of this invention.

The above summary is not intended to describe each illustrated embodiment or every implementation of the subject matter hereof. The figures and the detailed description that follow more particularly exemplify various embodiments.

DETAILED DESCRIPTION

Figure 1:
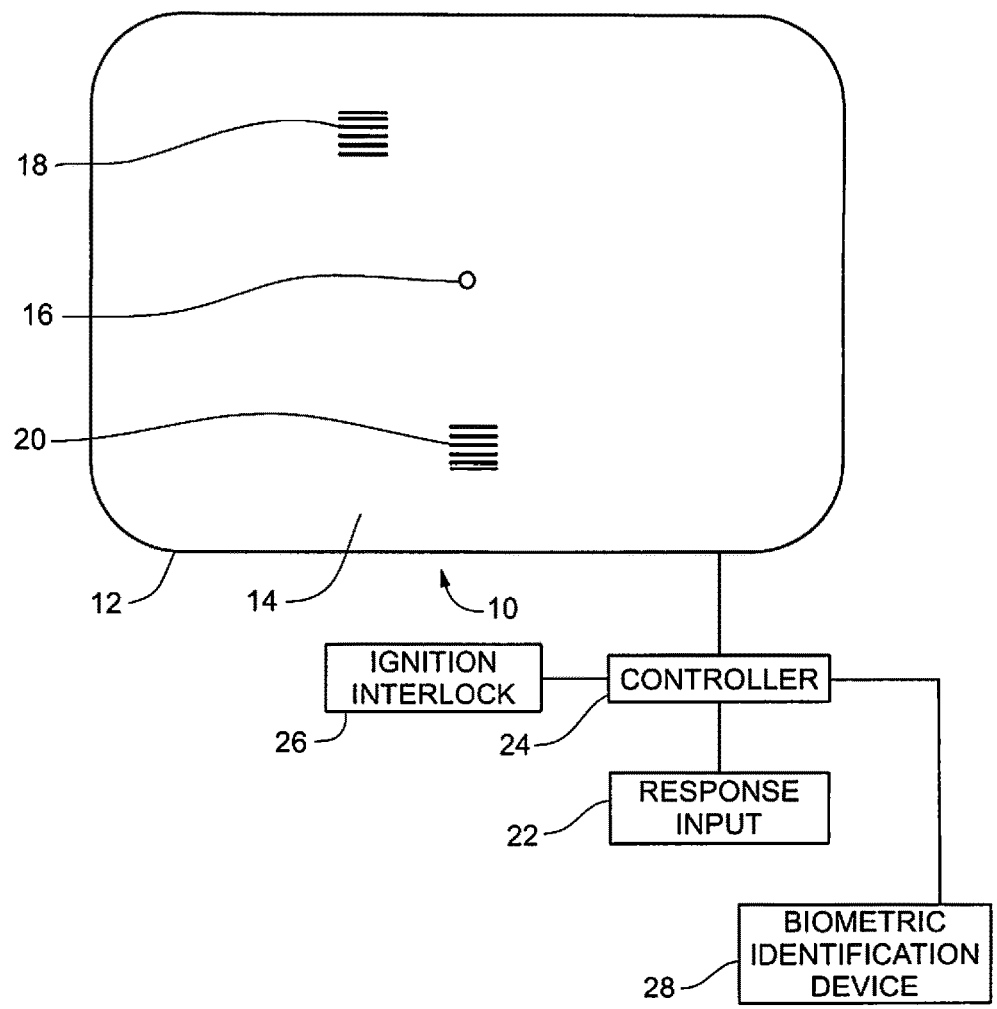
FIG. 1 is a depiction of a test screen according to an example embodiment of the invention.
Figure 2:
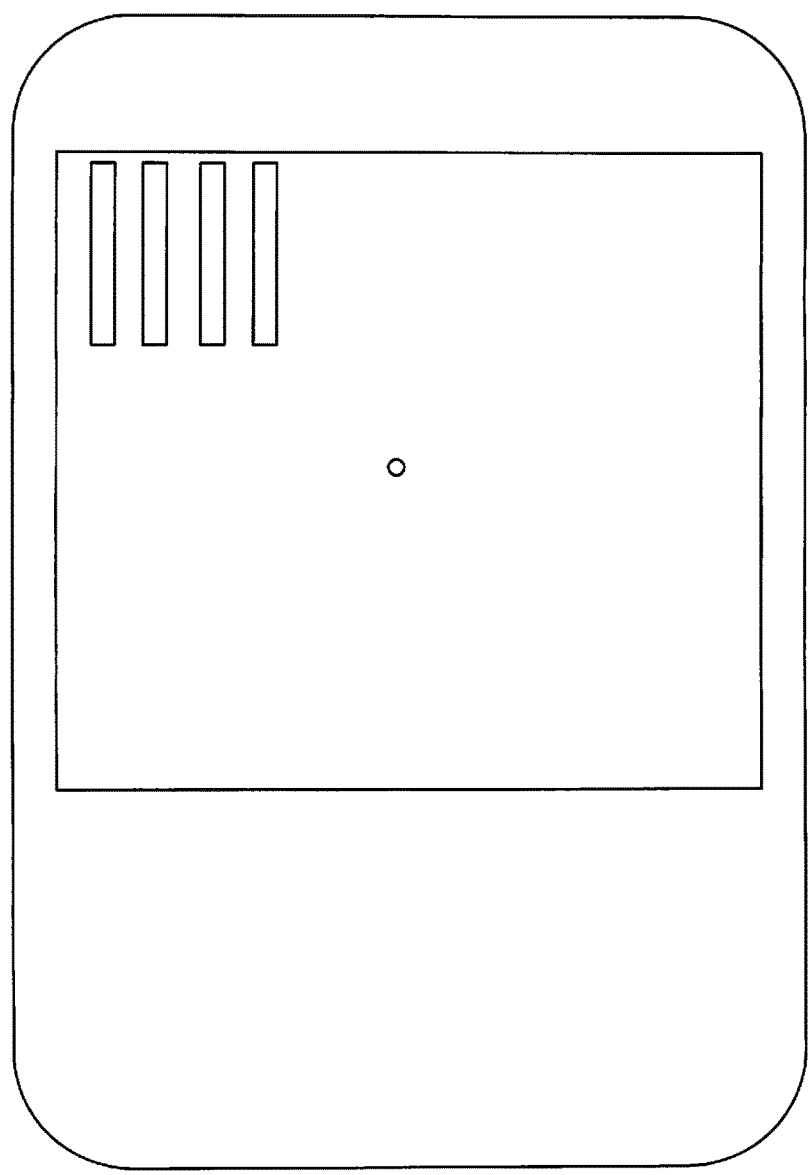
FIG. 2 is a depiction of a test screen according to another example embodiment of the invention.
Figure 3:
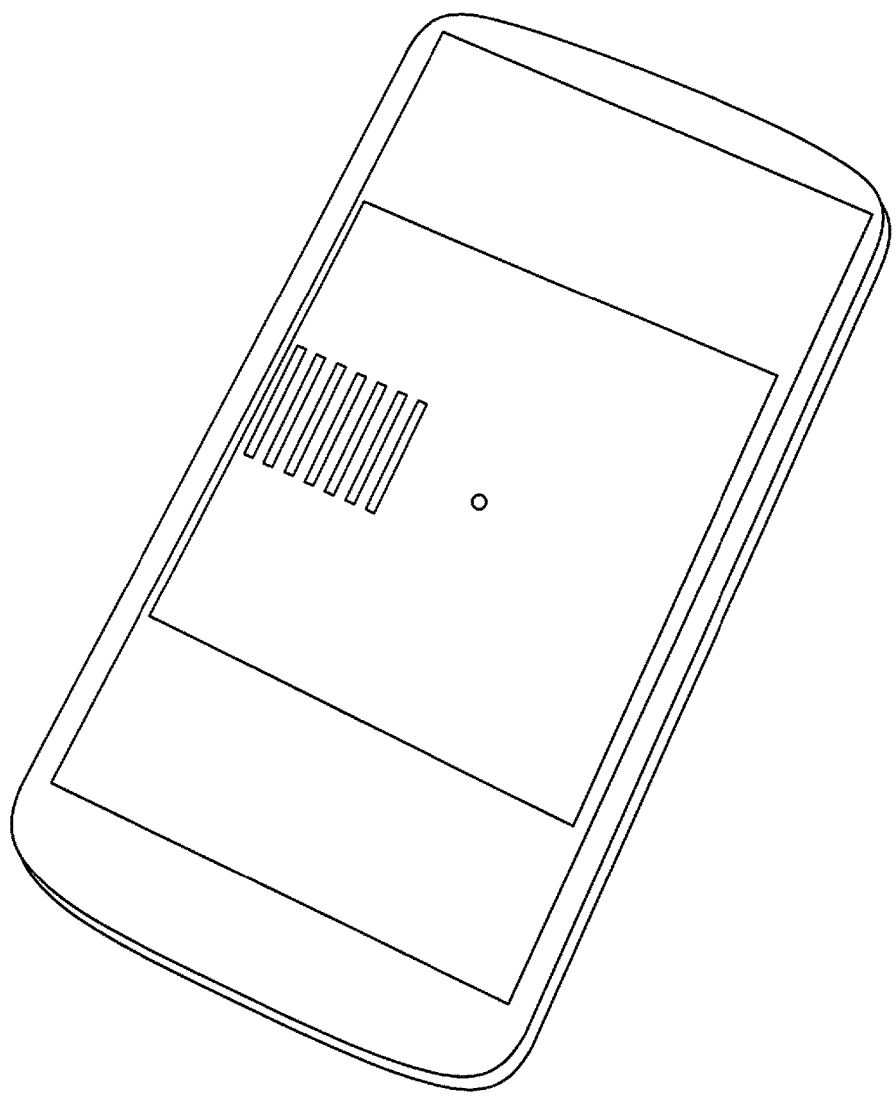
FIG. 3 is a depiction of a test screen according to a further example embodiment of the invention.

Referring to FIGS. 1, 2 and 3, test screen 10 according to an example embodiment of the invention is depicted. Test screen 10 includes perimeter 12, background field 14, fixation target 16, first sine wave grid 18 and second sine wave grid 20.

Background field 14 extends over the area within perimeter 12. Fixation target 16 is located approximately in the center of background field 14. Fixation target 16 may be any contrasting color to background field 14 and may be steady or flashing in nature First sine wave grid 18 and second sine wave grid 20 are representative of test targets presented during testing according to an example embodiment of the invention. First sine wave grid 18 and second sine wave grid 20 are presented at random locations within background field 14 peripheral to fixation target 16. The positions at which first sine wave grid 18 and second sine wave grid 20 are depicted represent two such random locations but many other random location are possible. First sine wave grid 18 and second sine wave grid 20 are presented in contrasting or complimentary colors including but not limited to, for example, black and white, red and green or blue and yellow.

Background field 14 is generally uniform in color and intensity. According to an example embodiment, background filed 14 is yellow in color but this should not be considered limiting.

Response input 22 is operably coupled to controller 24 and to test screen 10. Response input 22 may be integrated into a touch screen or may include a momentary contact switch operably y coupled to controller 24. Test screen 10 may be presented on a handholdable digital device such as a tablet, smartphone or a dedicated device. Controller 24 is typically included integrally in such a device and may include software, hardware or firmware including algorithms to operate the test.

According to a testing sequence of an example embodiment of the invention, a test subject is presented with a screen to be viewed either on a hand held digital device or in a virtual reality like headset. The subject fixates central fixation target 16 such as a contrasting dot. First sine wave grid 18 and second sine wave grid 20 are presented at random locations within background field 14 peripheral to fixation target 16. Various additional sine wave grating targets (not depicted) are presented randomly at locations peripheral to central fixation target 16 in background field 14. The test subject responds when, for example, first sine wave grid 18 is seen by activating response input 22. Testing continues as described elsewhere in this application until it is determined that the test subject is impaired or not impaired.

Ignition interlock 26 may be coupled to controller 24 and is operable as discussed elsewhere in this application.

Biometric identification device 28 may also be coupled to controller 24 and is operable as discussed elsewhere in this application. Biometric identification device 28 may include, for example, biometric iris recognition, fingerprint recognition or biometric retinal recognition.

Referring to FIGS. 2 and 3, test screens according to other example embodiments are depicted.

Figure 4:
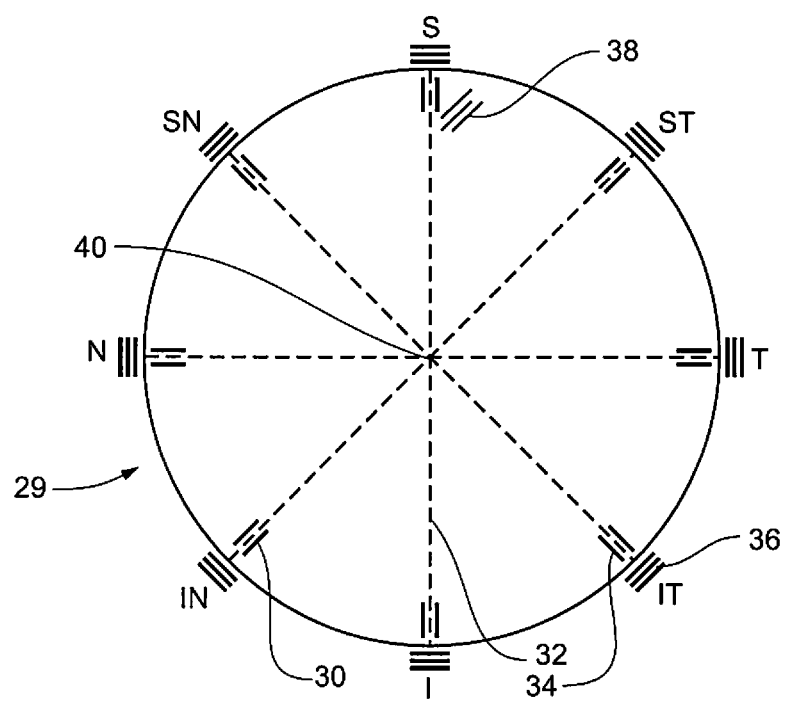
FIG. 4 is a schematic depiction of meridians of the eye or visual field and of gratings oriented parallel, perpendicular and oblique to the meridians.

Referring to FIG. 4, a schematic depiction of meridians of the eye or visual field 29 and of gratings 30 oriented parallel, perpendicular and oblique to meridians 32.

Meridians 32 include superior meridian S, superior temporal meridian ST, temporal meridian T, inferior temporal meridian IT, inferior meridian I, inferior nasal meridian IN, nasal meridian N, and superior nasal meridian SN.

Gratings 30 include meridian parallel gratings 34 and meridian perpendicular gratings 36 which are parallel or perpendicular to their respective meridians. Gratings 30 may also be presented as meridian oblique gratings 38.

Gratings 30 may be presented to the eye in a variety of orientations as discussed above. According to example embodiments of the invention, meridian parallel gratings 34 may be presented peripherally to fixation in orientations parallel to meridians 32, perpendicular to the meridians or oblique to the meridians. For the purposes of this disclosure meridians 32 should be considered to be lines that pass generally through point of fixation 40 and that radiate outwardly to the peripheral retina or peripheral visual field.

Gratings 30 may be presented parallel to meridians 32 with the intention of taking advantage of the meridional preference effect. Research has demonstrated that stimuli oriented radially, parallel to the meridian like meridian parallel gratings 34, are better resolved than stimuli in other orientations. Accordingly, the eye may demonstrate greater sensitivity to stimuli with meridian parallel gratings 34.

Alternatively, if comparison between two gratings 30 is desired, example embodiments of the invention may present meridian oblique gratings 38. For example meridian oblique gratings 38 may be presented at angles of plus and minus forty five degrees relative to meridians 32. This means that meridian oblique gratings 38 should be perceived with approximately equal sensitivity and facilitate comparison of the two stimuli presented by meridian oblique gratings 38.

Further aspects of embodiments of the invention are presented below.

1. A method of identifying individuals impaired by a psychoactive substance, the method comprising:
    presenting monocularly to a subject being tested; to each eye separately, a sinusoidal grating pattern of fixed spatial frequency with achromatic contrast or color contrast between grating stripes being temporally alternately modulated at a temporal frequency that ranges between 10 Hz and 60 Hz with a pattern of the contrast being such that the subject being tested can see a frequency doubling in the grating pattern;
    decreasing the contrast of the grating pattern presented until a first contrast ratio/value is reached wherein the frequency doubling in the grating pattern is no longer reported as being seen by the test subject;
    further decreasing the contrast of the grating pattern until a second contrast ratio/value is well below the test subject's threshold of detection of the second contrast ratio/value;
    increasing the contrast of the grating pattern until a third contrast ratio/value is reached where the frequency doubling in the grating pattern is first detectable;
    comparing the first contrast ratio/value and the third contrast ratio/value to a range of expected values of a normal population who have not consumed cannabis and have no pathology impacting the visual functions tested;
    if the first contrast ratio/value and the third contrast ratio/value are within the expected range of values then indicating that the test subject is not impaired; and
    if the first contrast ratio/value and the third contrast ratio/value are not within the expected range of values then indicating that the test subject is impaired.

2. The method as claimed in claim 1, further comprising varying the first contrast ratio/value identified and varying the temporally alternate modulation in a range from 10 Hz to 60 Hz and determining when the frequency doubling in the sinusoidal grating pattern is first detectable by the test subject.

3. The method as claimed in claim 1, further comprising varying the third contrast ratio/value identified and varying the temporally alternate modulation in a range from 10 Hz to 60 Hz and determining when the frequency doubling in the grating pattern is first detectable by the test subject.

4. The method as claimed in claim 1, further comprising comparing the values identified in claims 1-3 above to the contrast ratio values combined with temporal values in the modulation (alterations) and comparing them to those of a normal population who have not consumed cannabis and have no pathology impacting the functions tested.

5. The method as claimed in claimed in claim 1, further comprising determining a threshold by a procedure based on Bayesian statistics including Zippy Estimation of Sequential Testing (ZEST).

6. The method as claimed in claimed in claim 1, further comprising presenting the sinusoidal grating pattern achromatically.

7. The method as claimed in claim 1, further comprising presenting the sinusoidal grating pattern chromatically with alternate stripes being in complementary colors.

8. The method as claimed in claim 7, wherein the complementary colors comprise yellow and blue 9. The method as claimed in claim 7, wherein the complementary colors are matched in luminence.

10. The method as claimed in claim 8, wherein the sinusoidal grating pattern is presented on a yellow background.

11. The method as claimed in claim 7, further comprising temporally alternately modulating the contrast between grating stripes by varying a saturation of the stripes.

12. The method as claimed in claim 1, further comprising holding the spatial frequency and the temporal frequency fixed while varying the contrast or saturation.

13. The method as claimed in claim 1, further comprising a vehicle ignition interlock wherein if the test subject is found to be impaired the vehicle ignition interlock prevents operation of a motor vehicle.

14. The method as claimed in claim 13, further comprising obtaining biometric recognition wherein a user driving the vehicle is identified to be the test subject who took the test.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method of identifying individuals impaired by a psychoactive substance other than alcohol, the method comprising:
    presenting monocularly to a subject being tested; to each eye separately, a sinusoidal grating pattern of fixed spatial frequency with achromatic contrast or color contrast between grating stripes, the achromatic contrast or the color contrast between the grating stripes being temporally alternately modulated at a temporal frequency that ranges between 10 Hz and 60 Hz with a pattern of the contrast being such that the subject being tested can see a frequency doubling in the grating pattern thereby evaluating retinal function;

decreasing the contrast of the grating pattern presented until a first contrast ratio/value is reached wherein the frequency doubling in the grating pattern is no longer reported as being seen by the test subject;

further decreasing the contrast of the grating pattern until a second contrast ratio/value is below the test subject's threshold of detection of the second contrast ratio/value;

increasing the contrast of the grating pattern until a third contrast ratio/value is reached where the frequency doubling in the grating pattern is first detectable;

comparing the first contrast ratio/value and the third contrast ratio/value to a range of expected values of a normal population who have not consumed the psychoactive substance and have no pathology impacting retinal visual functions tested;

if the first contrast ratio/value and the third contrast ratio/value are within the range of expected values, then indicating that the test subject is not impaired; and if the first contrast ratio/value and the third contrast ratio/value are not within the range of expected values then indicating that the test subject is impaired.

2. The method as claimed in claim 1, further comprising varying the first contrast ratio/value identified and varying the temporally alternate modulation in a range from 10 Hz to 60 Hz and determining a frequency doubling value when the frequency doubling in the sinusoidal grating pattern is first detectable by the test subject.

3. The method as claimed in claim 1, further comprising varying the third contrast ratio/value identified and varying the temporally alternate modulation in a range from 10 Hz to 60 Hz and determining a frequency doubling value when the frequency doubling in the grating pattern is first detectable by the test subject.

4. The method as claimed in claim 2, further comprising comparing the frequency doubling temporal value values identified to the contrast ratio values combined with temporal values in the modulation (alterations) and comparing the frequency doubling temporal values to the temporal values of a normal population who have not consumed the psychoactive substance and have no pathology effecting the retinal visual functions tested.

5. The method as claimed in claim 3, further comprising comparing the frequency doubling temporal value values identified to the contrast ratio values combined with temporal values in the modulation (alterations) and comparing them to the temporal values of a normal population who have not consumed cannabis and have no pathology effecting the functions tested.

6. The method as claimed in claimed in claim 1, further comprising determining a threshold by a procedure based on Bayesian statistics including Zippy Estimation of Sequential Testing (ZEST).

7. The method as claimed in claim 1, further comprising presenting the sinusoidal grating pattern achromatically.

8. The method as claimed in claim 1, further comprising presenting the sinusoidal grating pattern chromatically with alternate stripes being in complementary colors.

9. The method as claimed in claim 8, wherein the complementary colors comprise yellow and blue.

10. The method as claimed in claim 8, wherein the complementary colors are matched in luminence.

11. The method as claimed in claim 9, wherein the sinusoidal grating pattern is presented on a yellow background.

12. The method as claimed in claim 8, further comprising temporally alternately modulating the contrast between grating stripes by varying a saturation of the stripes.

13. The method as claimed in claim 1, further comprising holding the spatial frequency and the temporal frequency fixed while varying a contrast or a saturation.

14. The method as claimed in claim 1, further comprising using a vehicle ignition interlock wherein if the test subject is found to be impaired the vehicle ignition interlock prevents operation of a motor vehicle.

15. The method as claimed in claim 14, further comprising obtaining biometric recognition wherein a user driving the vehicle is identified to be the test subject who took the test.

16. The method as claimed in claim 1, further comprising presenting the sinusoidal grating patterns at an oblique angle to an ocular meridian.

17. The method as claimed in claim 1, further comprising presenting the sinusoidal grating patterns at a parallel or perpendicular to an ocular meridian.

18. A device for identifying individuals impaired by a psychoactive substance other than alcohol, the device comprising:

a display on which images are displayed monocularly to a subject being tested; to each eye separately, the display presenting a sinusoidal grating pattern of fixed spatial frequency with contrast between the grating stripes being temporally alternately modulated at a temporal frequency that ranges between 10 Hz and 60 Hz with a pattern of the contrast being such that the subject being tested can see a frequency doubling in the grating pattern thereby evaluating retinal function;

the display being coupled to a processor that is programmed with an algorithm by which an operator can control the display to present the following procedure:

decreasing the contrast of the grating pattern presented until a first contrast ratio/value is reached wherein the frequency doubling in the grating pattern is no longer reported as being seen by the test subject;

further decreasing the contrast of the grating pattern until a second contrast ratio/value is below the test subject's threshold of detection of the second contrast ratio/value;

increasing the contrast of the grating pattern until a third contrast ratio/value is reached where the frequency doubling in the grating pattern is first detectable;

comparing the first contrast ratio/value and the third contrast ratio/value to a range of expected values of a normal population who have not consumed the psychoactive substance and have no pathology impacting the retinal visual functions tested;

if the first contrast ratio/value and the third contrast ratio/value are within the range of expected values, then indicating that the test subject is not impaired; and if the first contrast ratio/value and the third contrast ratio/value are not within the range of expected values then indicating that the test subject is impaired.

19. The device as claimed in claim 18, further comprising a vehicle ignition interlock wherein if the test subject is found to be impaired the vehicle ignition interlock prevents operation of a motor vehicle.

20. The device as claimed in claim 18, further comprising biometric recognition wherein a user driving the vehicle is identified to be the test subject who took the test.

* * * * *

UNITED STATES PATENT AND TRADEMARK OFFICE
CERTIFICATE OF CORRECTION

PATENT NO. : 10,448,821 B2
APPLICATION NO. : 15/297886
DATED : October 22, 2019
INVENTOR(S) : Denise A. Valenti Page 1 of 1

It is certified that error appears in the above-identified patent and that said Letters Patent is hereby corrected as shown below:

In the Claims

Column 15, Line 58, delete "claimed in"

Column 15, Line 62, delete "claimed in"

Signed and Sealed this
Fourteenth Day of April, 2020

Andrei Iancu
*Director of the United States Patent and Trademark Office*